United States Patent
Tu et al.

[19]

[11] Patent Number: 6,033,403
[45] Date of Patent: Mar. 7, 2000

[54] LONG ELECTRODE CATHETER SYSTEM AND METHODS THEREOF

[75] Inventors: Hosheng Tu; Cary Hata, both of Tustin, Calif.

[73] Assignee: Irvine Biomedical, Inc., Irvine, Calif.

[21] Appl. No.: 09/168,575

[22] Filed: Oct. 8, 1998

[51] Int. Cl.[7] .................................................. A61B 18/18
[52] U.S. Cl. ............................................ 606/41; 607/102
[58] Field of Search ........................ 606/41, 45, 48–50; 607/101, 102; 600/374

[56] References Cited

U.S. PATENT DOCUMENTS

| | | | |
|---|---|---|---|
| 4,532,924 | 8/1985 | Auth et al. ................................. | 606/50 |
| 5,766,171 | 6/1998 | Silvestrini ................................. | 606/49 |
| 5,863,291 | 1/1999 | Schaer ....................................... | 606/41 |
| 5,921,924 | 7/1999 | Avitall ...................................... | 600/374 |
| 5,921,982 | 7/1999 | Lesh et al. ................................ | 606/41 |
| 5,938,660 | 8/1999 | Swartz et al. ............................. | 606/45 |

*Primary Examiner*—Michael Peffley

[57] ABSTRACT

An improved catheter system having an electrode means at its tip section capable of delivering a long continuous linear lesion in tissues of a patient. A catheter system suitable for radiofrequency ablation of cardiac tissues comprising an electrode means mounted on the distal tip section of the catheter shaft, the electrode means having a wire and a plurality of ring electrodes, the wire having a wire core section, a wire distal end and a wire proximal end, wherein a first ring electrode is secured to the wire distal end and a second ring electrode is secured to the wire proximal end. The catheter system also comprises an external RF current generator, wherein a RF current is delivered to the electrode means.

20 Claims, 8 Drawing Sheets

LONG ELECTRODE CATHETER SYSTEM AND METHODS THEREOF

FIELD OF THE INVENTION

The present invention generally relates to improved constructions for a catheter system. More particularly, this invention relates to a catheter system and methods for ablating tissues via a steerable ablation catheter comprising a long electrode at its tip section, which has linear lesion capabilities.

BACKGROUND OF THE INVENTION

The heart includes a number of normal pathways that are responsible for the propagation of electrical signals from the upper to lower chambers necessary for performing normal systole and diastole function. The presence of an arrhythmogenic site or accessory pathway can bypass or short circuit the normal pathway, potentially resulting in very rapid heart contractions, referred to here as tachycardias.

A variety of approaches, including drugs, implantable pacemakers/defibrillators, surgery, and catheter ablation have been proposed to treat tachycardias. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols that have been proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablations tip electrode lies exactly at the target tissue site. Radiofrequency energy or other suitable energy, such as ultrasonic energy, laser energy, or microwave energy, is then applied through the tip electrode to the cardiac tissue in order to ablate the tissue of the arrhythmogenic site or the accessory pathway. By successfully destroying that tissue, the abnormal signal patterns responsible for the tachycardia may be eliminated. However, in the case of atrial fibrillation (AFib) or atrial flutter (AFlu), multiple arrhythmogenic sites and/or multiple accessory pathways exist. The conventional catheter with a single short ablation electrode can not effectively cure the symptoms.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

The tip section of a conventional electrophysiology catheter that is deflectable usually contains one large rigid electrode about 4 to 8 mm in length for ablation purposes. Because of the rigidity of the large electrode, the length is severely restricted. Sometimes, a plurality of long electrodes is used in creating a contiguous, non-continuous, linear lesion. In some clinical trials, the gap between two lesions is so large that it is not even considered as "contiguous".

Recently, a catheter system having a coil-type electrode has been used clinically. Though a coil-type electrode can be very long as a result of its flexibility properties, the resulting lesion from such a catheter is at best contiguous. The outermost ridge of each coil pass of the coil-type electrode contacts the tissue, wherein the distance between the ridges may only create a contiguous linear lesion. Furthermore, the overall outer surface of the catheter having a coil-type electrode is wavy or bumpy. Blood clotting has been observed at a low-flow spot of the coils, such as the hind side of the coils with respect to the bloodflow direction.

While a radiofrequency electrophysiology ablation procedure using an existing catheter has had promising results, the tip section of a known catheter usually has a rigid fixed-length electrode when contacting the tissue for ablation purposes. Therefore there is a need for an improved catheter and methods for making a linear and larger lesion in the cardiac tissue employing a flexible "long" electrode during ablation procedures.

SUMMARY OF THE INVENTION

In general, it is an object of the present invention to provide a flexible long electrode to a catheter. The "long electrode" is defined in this invention as an electrode that is flexible, and preferably deflectable, along with the catheter shaft in the axial direction with respect to the catheter shaft itself. The long electrode is different from the coil-type or mesh-type electrode, in which the contact line of a long electrode of the present invention with the tissue is continuous, not contiguous.

It is another object to provide a fluid infusion and irrigation capability to the long electrode portion of a catheter of the present invention. This capability of fluid infusion/irrigation may be applicable to the drug delivery means for treating tumors or cancers. The capability of fluid infusion and irrigation may be applicable to special means of cooling off the tissue contact site due to impedance rise as a result of ablation operation. The fluid may be selected from the group consisting of cold saline, saline, heparin, antibiotics, anti-inflammatory, chemotherapy and therapeutics fluids. To facilitate fluid infusion/irrigation in a tubular vessel location, it is another object of the present invention to provide a catheter system comprising a plurality of balloons at the distal tip section of the catheter system.

It is another object of the invention to provide an ablation catheter with a tip section of a catheter shaft having a flexible long electrode, wherein the flexible long electrode is comprised of a linear wire having a wire core section, a wire distal end, a wire proximal end, and a plurality of ring electrodes. A first ring electrode or a cap electrode is secured to the wire distal end while a second ring electrode is secured to the wire proximal end, wherein the wire stays intimately onto the catheter shaft. This catheter is particularly useful for treating a patient with AFib or AFlu as a result of its true long linear lesion.

An insulated conducting wire is connected to an external RF current generator for delivery of RF current to the electrode means during ablation operations and/or to an EKG monitor for recording and displaying of the endocardial or electrical signal measured by the electrode means.

A fluid source is positioned at one end of the catheter for supplying a fluid flow through the lumen of the said catheter shaft to the tip section. Therefore at ablation time, the tip section with an electrode means is positioned against the tissues to be ablated. The fluid is continuously or intermittently supplied through the passageway inside the lumen to evenly cover and rinse the electrode so that the impedance rise at the contact site is substantially reduced. Cooling off the electrode during RF current delivery results in optimal ablation efficiency and a desired deep and large lesion. The fluid can also be used to therapeutically treat the tissues.

The ablation catheter further comprises a steering mechanism at the handle for controlling the deflection of the said distal tip section having an electrode means. Usually a rotating ring or a push-pull plunger is employed in the steering mechanism. In another embodiment, the steerable ablation catheter comprises a multiple curve deflection of the tip section. One end of the steering wire is attached at certain point of the distal tip section of said catheter shaft. The other end is attached to the steering mechanism at the handle. The steering mechanism on a steerable catheter or device is well known to those who are skilled in the art.

At least one fluid conveying passageway is associated with the elongated catheter shaft, and is preferably disposed within the catheter shaft along the longitudinal axis thereof. The lumen is adapted to communicate with a fluid supply source to convey fluid from the source and through the lumen to be discharged out of the tip section containing a flexible, preferably deflectable, long electrode.

The invention also comprises a method and system for controlling the flow rate of fluid through the lumen to optimize the cooling effect of the energy-delivering electrode of the catheter system. The control system preferably regulates the flow rate based on signals representative of the temperature of the catheter tip and/or tissue impedance.

In a particular embodiment, a cap electrode is disposed at the tip section of the catheter shaft. One conducting wire which is soldered to said electrode passes through the lumen of the catheter shaft and the interior void of the handle and is thereafter soldered to a contact pin of the connector secured at the proximal end of the handle. Therefrom, the conducting wire is connected to an external RF generator for delivery of RF energy during ablation operations and/or to an EKG monitor for recording and displaying of the endocardial or epicardial electrical signal from the electrode.

In an additional embodiment, the ablation system further comprises a temperature sensing and closed-loop temperature control mechanism for the electrode having at least one temperature sensor at the tissue contact site of the electrode. The location of the temperature sensor is preferably in the very proximity of the electrode means. In a still further embodiment, a method for operating an ablation catheter further comprises a programmed temperature control mechanism for independently controlling the delivery of RF energy of each electrode of the ablation catheter.

In one embodiment, the material for the electrodes may consist of conductive metals such as platinum, iridium, gold, silver, stainless steel, Nitinol or an alloy of their mixture.

A method for operating an ablation catheter system having an electrode means of the present invention at the distal tip section contacts the interior wall within a heart chamber. The method comprises percutaneously introducing the catheter system through a blood vessel to the heart chamber, wherein the distal tip section comprises a flexible long electrode. The distal tip section of the catheter shaft is positioned on the interior wall of the heart chamber. Then applying RF energy to the electrode means for tissue ablation.

The catheter system of the present invention has several significant advantages over known catheters or ablation techniques. In particular, the electrode means of a steerable ablation catheter of this invention may result in a real linear lesion that is highly desirable in atrial flutter and atrial fibrillation treatments.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
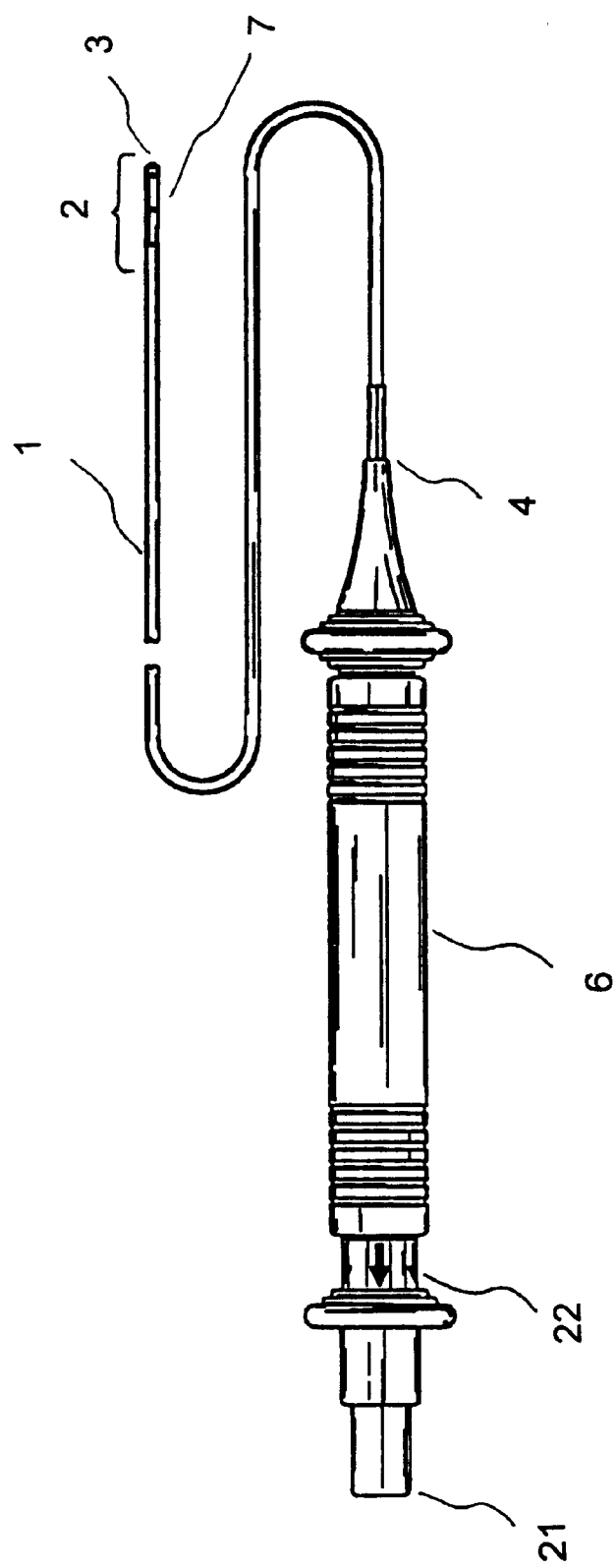
FIG. 1 is an overall view of a catheter system having a flexible long electrode means at its distal tip section constructed in accordance with the principles of the present invention.

FIG. 1 shows an overall view of a catheter system having a flexible long electrode means at its distal tip section constructed in accordance with the principles of the present invention. A catheter system comprises a catheter shaft 1 having a distal tip section 2, a shaft distal end 3, a shaft proximal end 4, and at least one lumen 5 extending between the shaft distal end 3 and shaft proximal end 4. A handle 6 is attached to the shaft proximal end 4 of the catheter shaft 1, wherein the handle 6 has a cavity. A wire electrode means 7 is mounted on the distal tip section 2 of the catheter shaft 1. The electrode means 7 has a wire means 8 and a plurality of ring 9, 10, wherein the wire means 8 has a wire core section 11, a wire distal end 12 and a wire proximal end 13. A first ring 10 is secured to the wire distal end 12 and a second ring 9 is secured to the wire proximal end 13. The wire means can be a flat wire, a meshed wire, and the like.

A connector 21 that is secured at the proximal end of the catheter system, is part of the handle 6. The handle has one optional uni-directional steering mechanism 22. The steering mechanism 22 is to deflect the tip section 2 of the catheter shaft 1 for catheter maneuvering and positioning. By deploying the steering mechanism 22, the distal tip section 2 of the catheter shaft 1 deflects to one direction. By un-deploying the steering mechanism 22, the tip section returns to its neutral position. In another embodiment, the steering mechanism 22 at the handle 6 comprises means for providing a plurality of deflectable curves on the distal tip section 2 of the catheter shaft 1. The mechanism of an ablation catheter having multiple flexible curves is described by a patent application Ser. No. 08/763,614, filed Dec. 11, 1996, now U.S. Pat No. 5,782,828.

Figure 2:
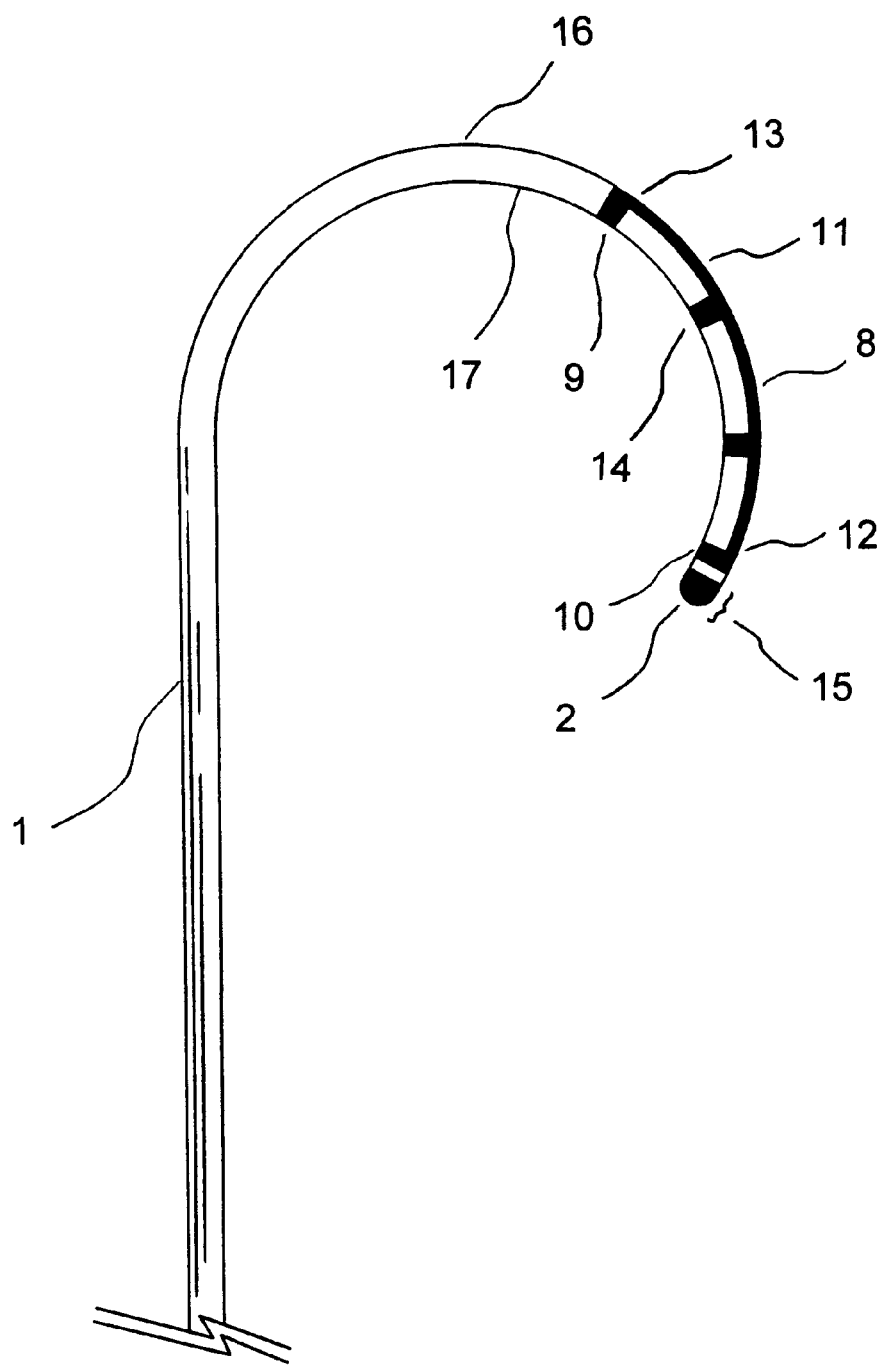
FIG. 2 is a close-up view of the distal tip section of the catheter system comprising a flexible long electrode means and a cap electrode at the distal end having linear lesion capabilities.

FIG. 2 shows a close-up view of the distal tip section 2 of the catheter system comprising a flexible long electrode means 7 and a cap 15 at the distal end 2 having linear lesion capabilities. The catheter system has an unidirectional deflectability. Under a deployed state, an outermost portion 16 of the catheter shaft surfaces lies in exact opposite to an innermost portion 17 of the catheter shaft 1. The catheter system further comprises at least one third ring 14 of the plurality of ring electrodes, wherein the at least one third ring 14 is secured to the wire core section 11 of the electrode means 7. In one embodiment, the wire is a flat wire. In another embodiment, the catheter system further comprises a cap electrode 15 at the shaft distal end 2 of the catheter shaft.

Figure 3:
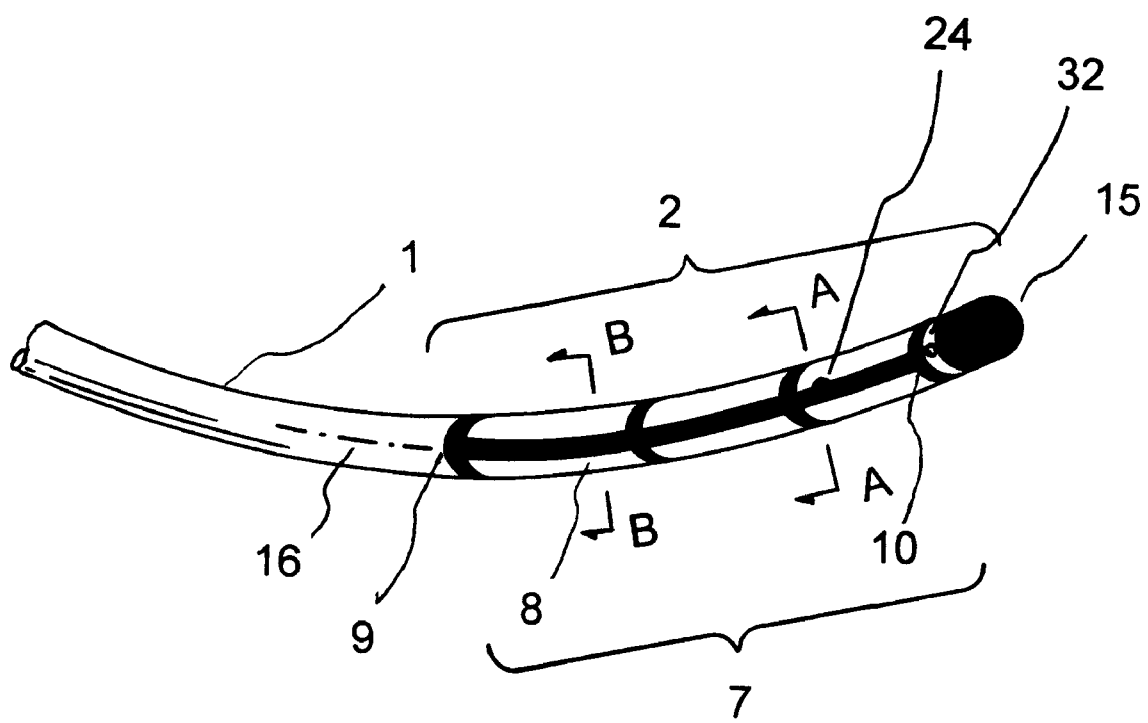
FIG. 3 is a perspective view of the electrode means of FIG. 2, wherein the wire of the flexible long electrode is located at the outermost portion of the deflectable catheter shaft of the present catheter system.

FIG. 3 shows a perspective view of the electrode means of FIG. 2, wherein the wire 8 of the flexible long electrode 7 is located at the outermost portion 16 of the deflectable catheter shaft of the present catheter system.

Figure 4:
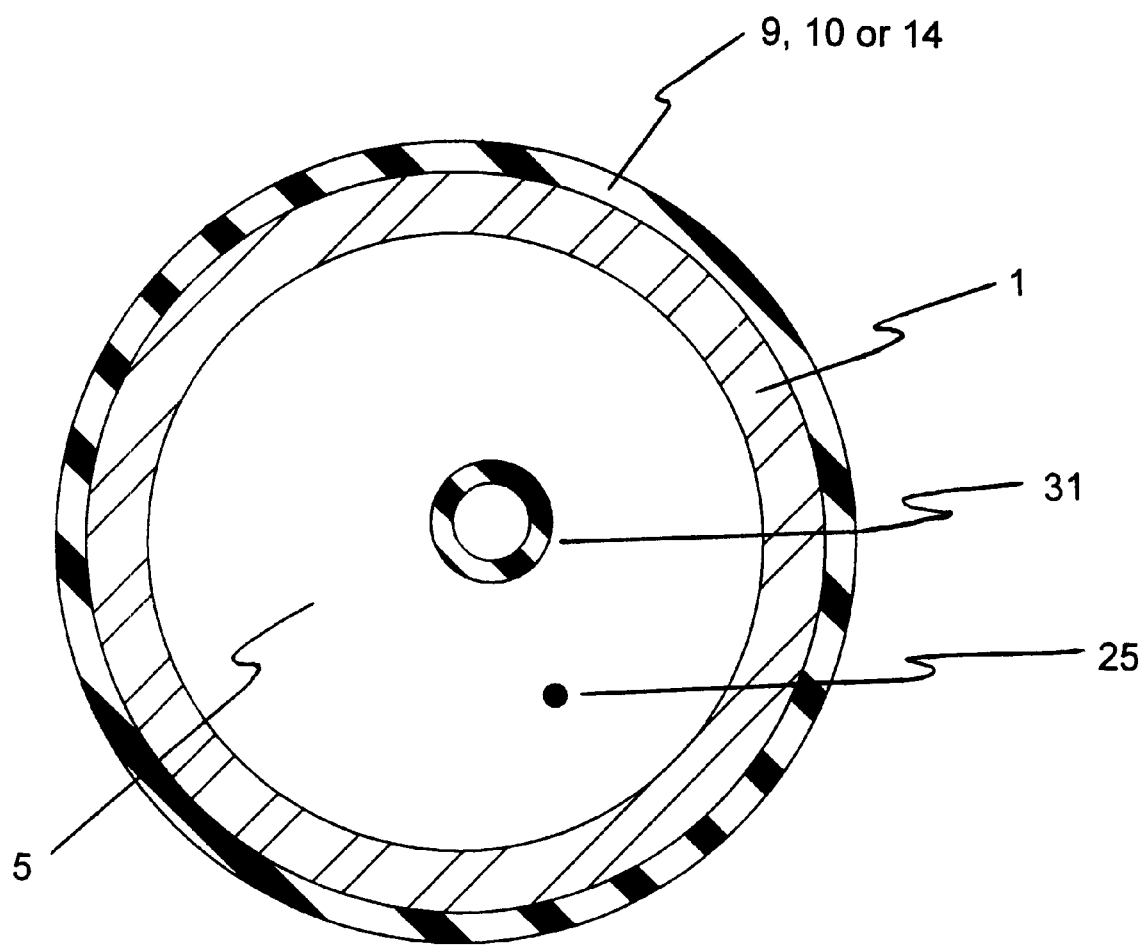
FIG. 4 is a cross-sectional view of the ring electrode portion, section A—A, of the distal tip section of FIG. 3.
Figure 5:
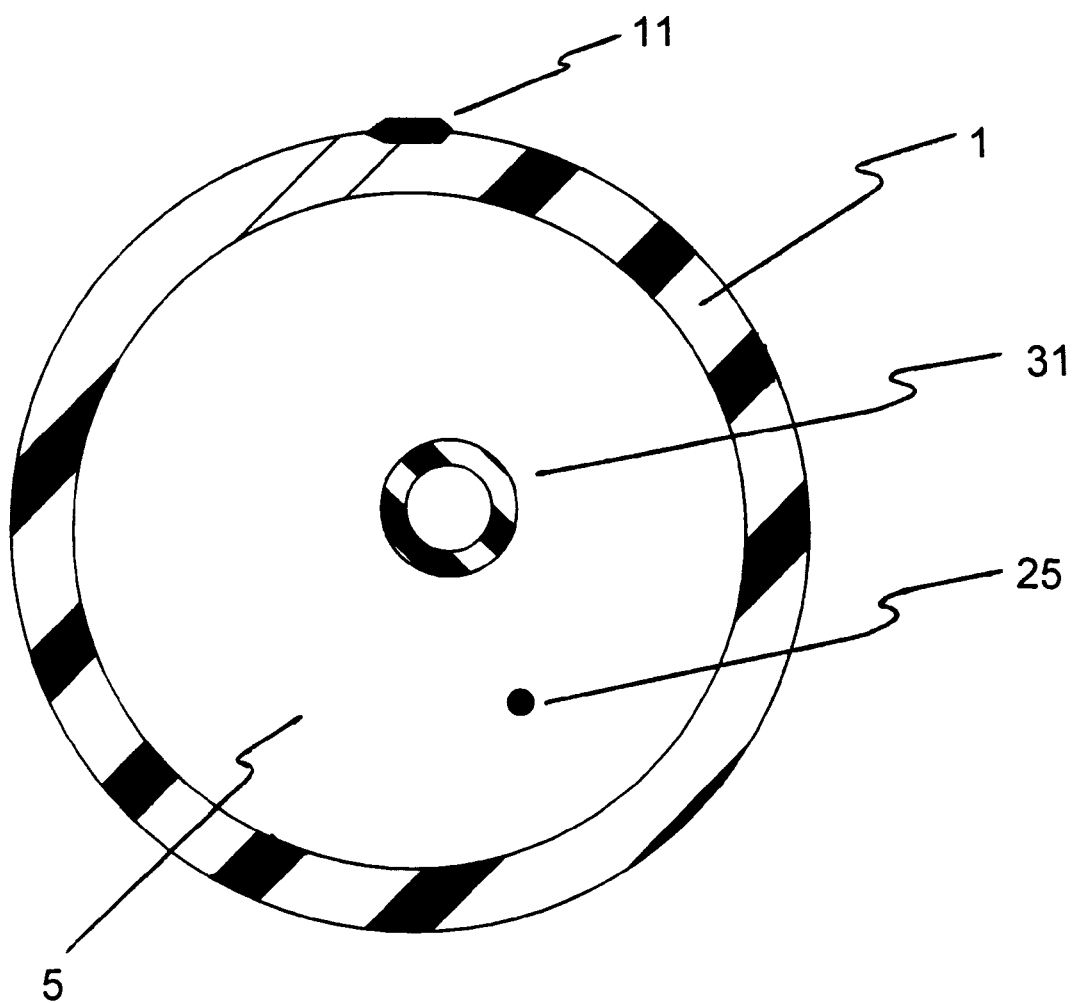
FIG. 5 is a cross-sectional view of the non-ring electrode portion, section B—B, of the distal tip section of FIG. 3.

FIG. 4 shows a cross-sectional view of the ring electrode portion, section A—A of FIG. 3, of the distal tip section 2 of the catheter shaft 1. The ring 9, 10 or 14 covers a majority of the circumference of the catheter shaft I. FIG. 5 shows a cross-sectional view of the non-ring electrode portion, section B—B of FIG. 3, of the distal tip section 2 of the catheter shaft 1. The core wire portion 11 of the wire 8 of the electrode means 7 stays intimately onto the shaft surface.

In one embodiment, a fluid conveying passageway 31 is associated with the catheter shaft 1, and is preferably disposed within the lumen 5 of the catheter shaft 1 along the longitudinal axis thereof. The fluid conveying passageway is adapted to communicate with a fluid supply source (not shown) to convey fluid from the source and through said passageway to be discharged out of the tip section 2 at an opening 32. The fluid flow rate from the fluid infusion mechanism may be between approximately 5 ml/min to 20 ml/min. The electrodes are formed of conducting materials selected from the group of platinum, iridium, gold, silver, stainless steel, and Nitinol.

Figure 6:
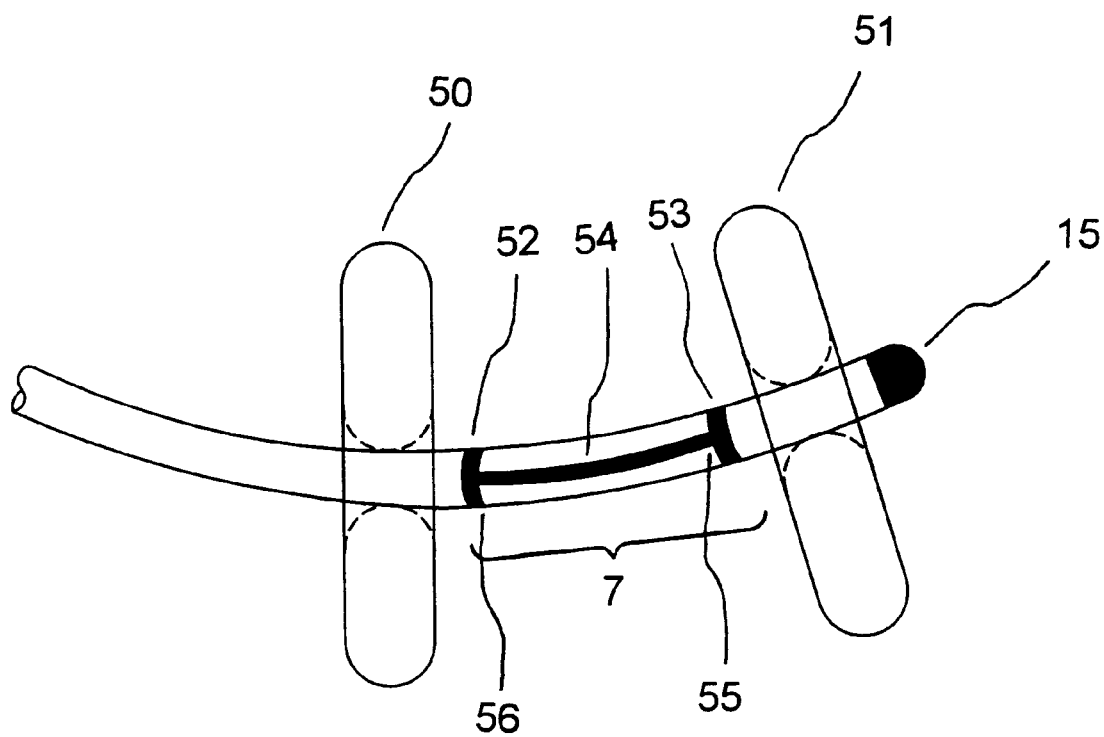
FIG. 6 is a perspective view of FIG. 2, comprising a flexible long electrode means and a plurality of balloons at the distal tip section of the present catheter system.

FIG. 6 shows a perspective view of the distal tip section 2 of an alternate catheter system comprising a plurality of balloons 50, 51 when deployed and a flexible long electrode 7 and a cap electrode 15. The balloons are made of materials selected from the group of compliant and non-compliant plastics, such as polyethylene, polyethylene terephthalate, polypropylene, nylon and the like. The catheter system comprises a catheter shaft 1 having a distal tip section 2, a shaft distal end 3, a shaft proximal end 4, and at least one lumen 5 extending between the shaft distal end 3 and shaft proximal end 4. A handle 6 is attached to the shaft proximal end 4 of the catheter shaft 1. The handle 6 has a cavity. The wire electrode means 7 has a wire 8, and at least one proximal ring 52 and one distal ring 53, the wire having a wire core section 54, a wire distal end 55 and a wire proximal end 56, wherein the at the least one proximal ring electrode 52 is secured to the wire proximal end 56 and the at least one distal ring 53 is secured to the wire distal end 55. The balloons are deployable by a fluid infusion/suction controller at the handle 6, wherein the balloons are used to block and isolate the region for ablation purposes.

Figure 7:
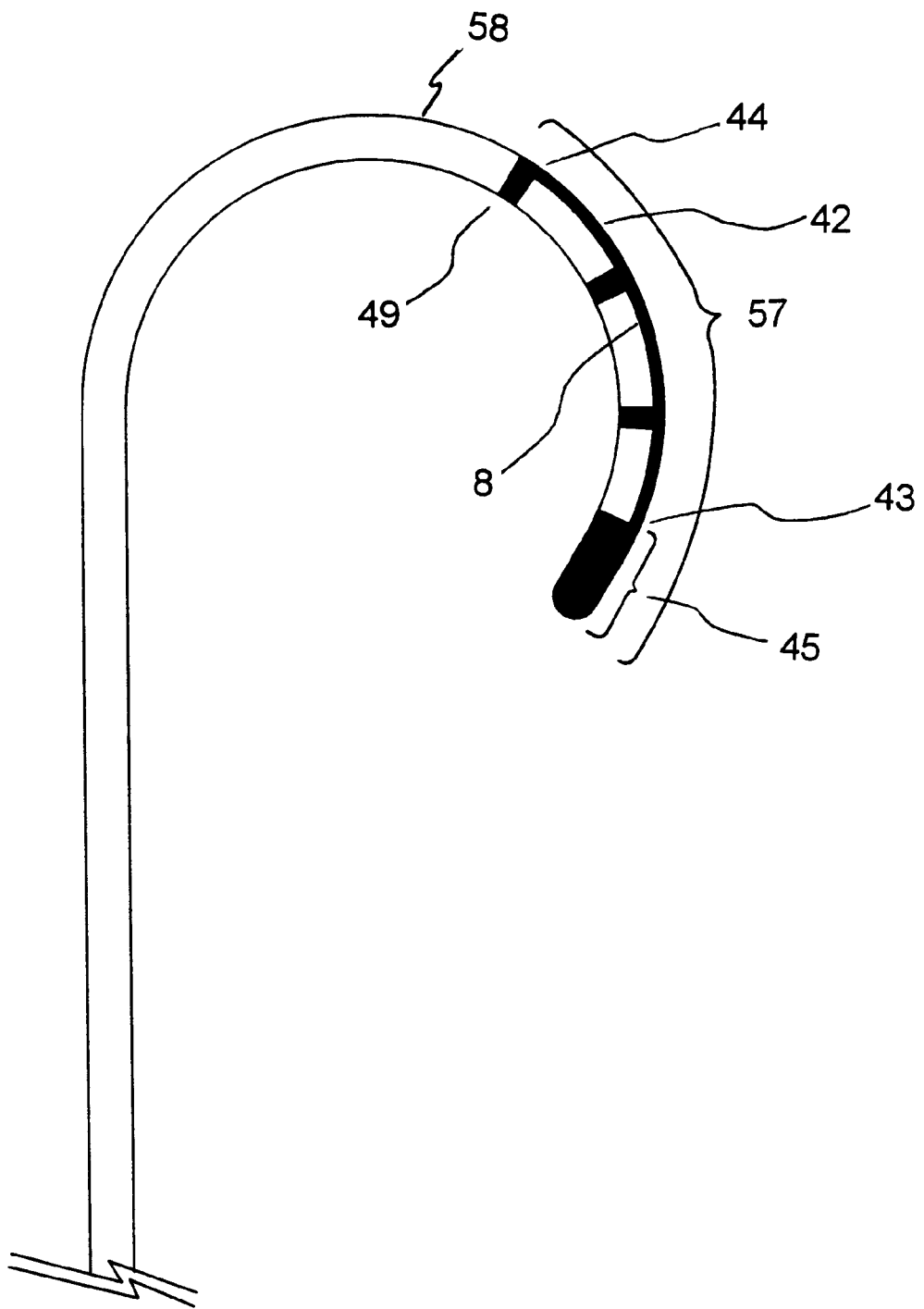
FIG. 7 is a close-up view of the distal tip section of an alternate catheter system comprising a flexible long electrode means having a cap electrode at the distal end having linear lesion capabilities.

FIG. 7 shows a close-up view of the distal tip section 2 of an alternate catheter system comprising a flexible long electrode means having a cap electrode at the distal end having linear lesion capabilities. The catheter system comprises a catheter shaft 1 having a distal tip section 2, a shaft distal end 3, a shaft proximal end 4, and at least one lumen 5 extending between the shaft distal end 3 and shaft proximal end 4. A handle 6 is attached to the shaft proximal end 4 of the catheter shaft 1. The handle 6 has a cavity. A wire electrode means 57 is mounted on the distal tip section 2 of the catheter shaft 1. The electrode means has a wire 8, a cap 45, and at least one ring 49, the wire having a wire core section 42, a wire distal end 43 and a wire proximal end 44, wherein the cap 45 is secured to the wire distal end 43 and the at least one ring 49 is secured to the wire proximal end 44.

Figure 8:
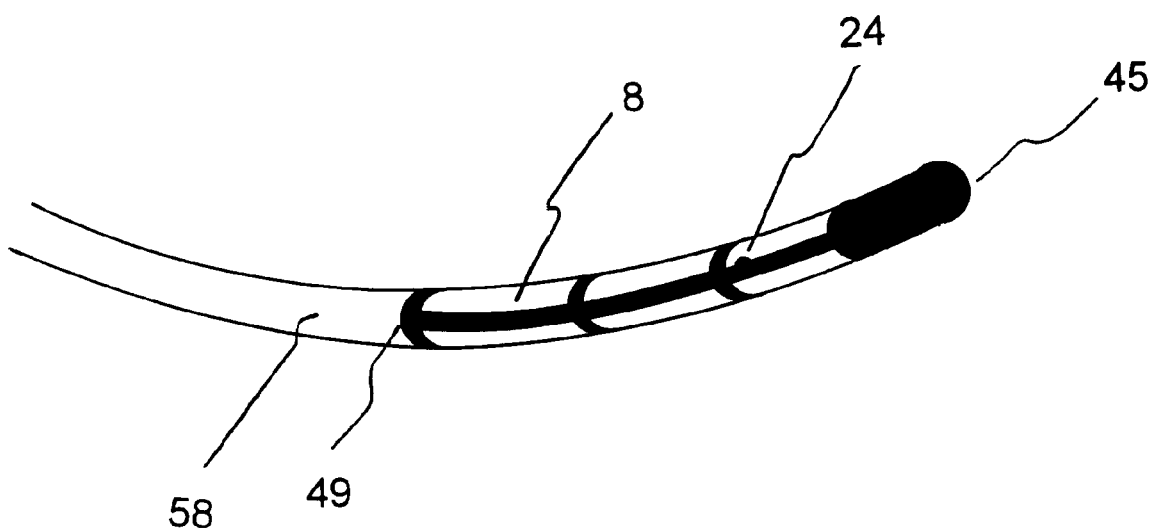
FIG. 8 is a perspective view of the electrode means of FIG. 5, wherein the flexible long electrode is located at the outermost portion of the deflectable catheter shaft of the present catheter system.

FIG. 8 shows a perspective view of the electrode means of FIG. 7, wherein the wire 8 of the electrode means 57 is located at the outermost portion 58 of the deflectable catheter shaft of the present catheter system.

The at least one ring electrode 9 or 10, has an insulated conducting wire (not shown) secured to the ring, which passes through the lumen of the catheter shaft 1 and is soldered to a contact pin of the connector 21 at the proximal end of the handle 6. The conducting wire from the end of the connector is externally connected to an EKG monitor for diagnosis or to a RF generator during an electrophysiology ablation procedure. Therefrom, the RF current is transmitted through the conducting wire to the electrode and the RF current is delivered to the target tissue for a true linear lesion.

A temperature sensor 24, either a thermocouple means or a thermister means, is constructed at the proximity of the electrode 9 or 10 to measure the tissue contact temperature when RF energy is delivered. The temperature sensing wire 25 from the thermocouple or thermister is connected to one of the contact pins (not shown) of the connector 21 and externally connected to a transducer and to a temperature controller. The temperature reading is thereafter relayed to a closed-loop control mechanism to adjust the RF energy output. The RF energy delivered is thus controlled by the temperature sensor reading or by a pre-programmed control algorithm.

In one embodiment, the catheter of this invention is meant to provide fluid communication and commensurate flow of fluid originating inside the tip section of the catheter shaft to the electrode exterior surface, which directs the fluid flow from inside the catheter shaft over the exterior surface of the electrode to provide a fluid protective layer surrounding the electrode to minimize temperature elevation of the electrode with biological tissues.

From the foregoing, it should now be appreciated that an improved catheter system having a long electrode at its tip section, which has linear lesion capabilities and an optional fluid infusion and irrigation capability has been disclosed for ablation procedures, including endocardial, epicardial, or body tissue. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
   a catheter shaft having a distal tip section, a shaft distal end, a shaft proximal end, and at least one lumen extending between the shaft distal end and shaft proximal end;
   a handle attached to the shaft proximal end of the catheter shaft, wherein the handle has a cavity; and
   a wire electrode means for treating tissue mounted on the distal tip section of the catheter shaft, the electrode means having a wire means for connecting a plurality of rings mounted on the catheter shaft, wherein the wire means is placed intimately at an outer surface of the catheter shaft and constitutes a long wire electrode that is secured to the catheter shaft by the plurality of rings, the wire means having a wire core section, a wire distal end and a wire proximal end, wherein a first ring of the plurality of rings is secured to the wire distal end and a second ring is secured to the wire proximal end.

2. The catheter system of claim 1, wherein at least a third ring of the plurality of rings is secured to the wire core section of the wire electrode means.

3. The catheter system of claim 1 wherein the wire means is a flat wire.

4. The catheter system of claim 1 further comprising a cap electrode at the shaft distal end of the catheter shaft.

5. The catheter system as in claim 1 further comprising at least one fluid passageway within the at least one lumen of the catheter shaft, wherein a fluid is supplied to and disposed out of the distal tip section of the catheter shaft.

6. The catheter system of claim 5 wherein the fluid is selected from the group consisting of saline, heparin, antibiotics, anti-inflammatory, chemotherapy and therapeutic fluids.

7. The catheter system as in claim 1 further comprising a steering mechanism at the handle for controlling the deflection of the distal tip section of the catheter system.

8. The catheter system as in claim 1 further comprising a RF current generator, wherein a RF current is delivered to the wire electrode means of the catheter system.

9. The catheter system as in claim 8 further comprising a temperature sensing means at the distal tip section of the catheter shaft, wherein the temperature sensing means is to measure and monitor a temperature.

10. The catheter system as in claim 1 further comprising a plurality of balloons secured on the catheter shaft.

11. A method for operating an ablation catheter system inside a cardiovascular circulatory system, the catheter system comprising a catheter shaft having a distal tip section, a shaft distal end, a shaft proximal end, and at least one lumen extending between the shaft distal end and shaft proximal end; a handle attached to the shaft proximal end of the catheter shaft, wherein the handle has a cavity; a wire electrode means for treating tissue mounted on the distal tip section of the catheter shaft, the electrode means having a wire means for connecting a plurality of rings mounted on the catheter shaft, wherein the wire means is placed intimately at an outer surface of the catheter shaft and constitutes a long electrode that is secured to the catheter shaft by the plurality of rings, the wire means having a wire core section, a wire distal end and a wire proximal end, wherein a first ring of the plurality of rings is secured to the wire distal end and a second ring is secured to the wire proximal end; and a RF current generator; the method comprising the steps of:

(a) percutaneously introducing the catheter system through a blood vessel at an appropriate vessel-cut point to a cardiovascular circulatory system;
   (b) positioning the electrode means of the distal tip section of the catheter shaft; and
   (c) applying RF current to the electrode means of the catheter shaft.

12. The method for operating an ablation catheter system inside a cardiovascular circulatory system as in claim 11, the catheter system further comprising a plurality of balloons secured on the catheter shaft, and the method further comprising deploying the plurality of balloons prior to applying RF current to the wire electrode means of the catheter shaft.

13. A catheter system comprising:
    a catheter shaft having a distal tip section, a shaft distal end, a shaft proximal end, and at least one lumen extending between the shaft distal end and shaft proximal end;
    a handle attached to the shaft proximal end of the catheter shaft, wherein the handle has a cavity; and
    a wire electrode means for treating tissue mounted on the distal tip section of the catheter shaft, the electrode means having a wire means for connecting a cap and at least one ring, the wire means having a wire core section, a wire distal end and a wire proximal end, wherein the cap is secured to the wire distal end and the at least one ring is secured to the wire proximal end, wherein the wire means is placed intimately at an outer surface of the catheter shaft and constitutes a long electrode that is secured to the catheter shaft by the cap and by the at least one ring.

14. The catheter system of claim 13, wherein one of the at least one ring is secured to the wire core section of the wire electrode means.

15. The catheter system of claim 13, wherein the wire means is a flat wire.

16. The catheter system as in claim 13 further comprising a fluid passageway within the at least one lumen of the catheter shaft, wherein a fluid is supplied to and disposed out of the distal tip section of the catheter shaft.

17. The catheter system as in claim 13 further comprising a steering mechanism at the handle for controlling the deflection of the distal tip section of the catheter system.

18. The catheter system as in claim 13 further comprising a RF current generator, wherein a RF current is delivered to the wire electrode means of the catheter system.

19. The catheter system as in claim 18 further comprising a temperature sensing means at the distal tip section of the catheter shaft, wherein the temperature sensing means is to measure and monitor a temperature.

20. A method for operating an ablation catheter system contacting an interior wall within a heart chamber, a catheter shaft having a distal tip section, a shaft distal end, a shaft proximal end, and at least one lumen extending between the shaft distal end and shaft proximal end; a handle attached to the shaft proximal end of the catheter shaft, wherein the handle has a cavity; a wire electrode means for treating tissue mounted on the distal tip section of the catheter shaft, the electrode means having a wire means for connecting a cap and at least one ring, the wire means having a wire core section, a wire distal end and a wire proximal end, wherein the cap is secured to the wire distal end and the at least one ring is secured to the wire proximal end, wherein the wire means is placed intimately at an outer surface of the catheter shaft and constitutes a long electrode that is secured to the catheter shaft by the cap and the at least one ring; and a RF current generator;

the method comprising the steps of:

(a) percutaneously introducing the catheter system through a blood vessel to a heart chamber;

(b) positioning the distal tip section of the catheter shaft on the interior wall of the heart chamber; and (c) applying RF current to the electrode means of the catheter shaft.

* * * * *